(12) United States Patent
Gharizadeh

(10) Patent No.: US 8,304,184 B2
(45) Date of Patent: Nov. 6, 2012

(54) GENOTYPING USING MULTIPLE VARIANT-SPECIFIC PRIMER POOLS

(76) Inventor: Baback Gharizadeh, Palo Alto, CA (US)

( * ) Notice: Subject to any disclaimer, the term of this patent is extended or adjusted under 35 U.S.C. 154(b) by 393 days.

(21) Appl. No.: 12/492,021

(22) Filed: Jun. 25, 2009

(65) Prior Publication Data

US 2010/0196888 A1 Aug. 5, 2010

Related U.S. Application Data

(63) Continuation-in-part of application No. 10/623,458, filed on Jul. 17, 2003, now abandoned.

(60) Provisional application No. 60/399,357, filed on Jul. 30, 2002.

(51) Int. Cl.
 *C12Q 1/68* (2006.01)
(52) U.S. Cl. ......................................................... 435/6.1
(58) Field of Classification Search .................... None
 See application file for complete search history.

(56) References Cited

U.S. PATENT DOCUMENTS 5,582,989 A * 12/1996 Caskey et al. ................. 435/6.18

FOREIGN PATENT DOCUMENTS

| EP | 402 132 | 12/1990 |
|---|---|---|
| WO | WO 96/06187 | 2/1996 |
| WO | WO 9606187 A1 * | 2/1996 |
| WO | WO 02/08460 | 1/2002 |

OTHER PUBLICATIONS

Ye et al. (Hum Mutat. Apr. 2001;17(4):305-16).*
Pourmand et al. (Nucleic Acids Res. Apr. 1, 2002;30(7):e31).*
Alderborn et al. (Genome Res. Aug. 2000;10(8)1249-58).*
Ronaghi (Anal Biochem. Nov. 15, 2000;286(2):282-8).*
Jacobs et al. (J Clin Microbiol. Mar. 1997;35(3):791-5).*
O'Meara et al. (J Clin Microbiol. Feb. 2001;39(2):464-73).*
Bray et al., "High-throughout multiplex SNP genotyping with MALDI-TOF mass spectrometry: practice, problems and promis", Hum. Mutat. 17, pp. 296-304 (2001).
Gharizadeh et al., "Multiple group-specific sequencing primers for reliable and rapid DNA sequencing", Molecular and Cellular Probes 17 (2003) pp. 203-210.
Gharizadeh et al., "Multiple primer DNA sequencing method", Electrophoresis 24, (2003) pp. 1145-1151.
Gharizadeh et al., "Sentinel-base DNA genotyping using multiple sequencing primers for high-risk human papillomaviruses", Molecular and Cellular Probes XX, (2006) pp. 1-9.
Gharizadeh et al., "Type-Specific Multiple Sequencing Primers", J. of Molecular Diagnostics, vol. 7, No. 2, (2005) pp. 198-205.
Makridakis et al., "Multiplex automated primer extension analysis: simultaneous genotyping of several polymorphisms", Biotechniques 31, pp. 1374-1380 (2001).
Pourmand et al. "Multiplex Pyrosequencing", Nucleic Acids Research, vol. 30, No. 7, 5 pgs. (2002).
Rady et al., "Type-specific primer-mediated direct sequencing of consensus primer-gnerated PCR amplicons of human papillomaviruses: a new approach for the simultaneous detection of multiple viral type infections", J. Virol Methods 53, pp. 245-254 (1995).
Rady et al.,"Direct sequencing of consensus primer generated PCR fragments of human papillomaviruses" J. Virol Methods 43, pp. 335-350 (1993).
Ye et al., "Fluorescent microsphere-based readout technology for multiplexed human single nucleotide polymorphism analysis and bacterial identification", Hum. Mutat. 17, pp. 305-316 (2001).

\* cited by examiner

*Primary Examiner* — Christopher M. Babic
(74) *Attorney, Agent, or Firm* — Squire Sanders (US) LLP

(57) ABSTRACT

This invention relates to the identification of variants of an organism using variant-specific oligonucleotide primer pools to specifically hybridize to those polynucleotides in an sample comprising a plurality of polynucleotides that contain a target sequence that is unambiguously identifiable with a particular variant of the organism.

14 Claims, 12 Drawing Sheets

SEQUENCE LISTING

<160> NUMBER OF SEQ ID NOS: 24

<210> SEQ ID NO 1
<211> LENGTH: 20
<212> TYPE: DNA
<213> ORGANISM: Human papillomavirus type 16

<400> SEQUENCE: 1
gctgccatat ctacttcaga        20

<210> SEQ ID NO 2
<211> LENGTH: 20
<212> TYPE: DNA
<213> ORGANISM: Human papillomavirus type 18

<400> SEQUENCE: 2
gcttctacac agtctcctgt        20

<210> SEQ ID NO 3
<211> LENGTH: 20
<212> TYPE: DNA
<213> ORGANISM: Human papillomavirus type 31

<400> SEQUENCE: 3
gtgctgcaat tgcaaacagt        20

<210> SEQ ID NO 4
<211> LENGTH: 20
<212> TYPE: DNA
<213> ORGANISM: Human papillomavirus type 33

<400> SEQUENCE: 4
acacaagtaa ctagtgacag        20

<210> SEQ ID NO 5
<211> LENGTH: 20
<212> TYPE: DNA
<213> ORGANISM: Human papillomavirus type 45

<400> SEQUENCE: 5
tatgtgcctc tacacaaaat        20

<210> SEQ ID NO 6
<211> LENGTH: 21
<212> TYPE: DNA
<213> ORGANISM: Human papillomavirus type 6

<400> SEQUENCE: 6
gtgcatccgt aactacatct t        21

<210> SEQ ID NO 7
<211> LENGTH: 21
<212> TYPE: DNA
<213> ORGANISM: Human papillomavirus type 11

<400> SEQUENCE: 7
gtgcatctgt gtctaattct g        21

<210> SEQ ID NO 8
<211> LENGTH: 23
<212> TYPE: DNA
<213> ORGANISM: Artificial Sequence
<220> FEATURE:

```
<223> OTHER INFORMATION: Primer

<400> SEQUENCE: 8
tttgttactg tggtagatac tac                                              23

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
gaaaaataaa ctgtaaatca tatt                                             24

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
cgtccmarrg gawactgatc                                                  20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gcmcagggwc ataayaatgc                                                  20

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
gctggcacgt agttagccg                                                   19

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gttagccggt gcttcttctg                                                  20

<210> SEQ ID NO 14
<211> LENGTH: 22
<212> TYPE: DNA
<213> ORGANISM: Artificial Sequence
<220> FEATURE:
<223> OTHER INFORMATION: Artificiall RNA sequence for testing purposes

<400> SEQUENCE: 14
gcggcacgga gagccgggcc cg                                               22

<210> SEQ ID NO 15
```

```
<211> LENGTH: 15
<212> TYPE: RNA
<213> ORGANISM: Artificial Sequence
<220> FEATURE:
<223> OTHER INFORMATION: Artificial RNA sequence for testing purpose

<400> SEQUENCE: 15
gcggcacgag agccg                                                          15

<210> SEQ ID NO 16
<211> LENGTH: 51
<212> TYPE: DNA
<213> ORGANISM: Escherichia coli

<400> SEQUENCE: 16
gctggcacgg agtagccggt gcttcttctg cgggtaacgt caatgagcaa a                  51

<210> SEQ ID NO 17
<211> LENGTH: 36
<212> TYPE: DNA
<213> ORGANISM: Escherichia coli

<400> SEQUENCE: 17
cgggtaacgt caatgagcaa aggtattaac tttact                                   36

<210> SEQ ID NO 18
<211> LENGTH: 63
<212> TYPE: DNA
<213> ORGANISM: Streptococcus pneumoniae

<400> SEQUENCE: 18
gctggcacgt agttagccgc cctttctggt aagataccgt cacagtgtga actttccact         60
ctc                                                                       63

<210> SEQ ID NO 19
<211> LENGTH: 45
<212> TYPE: DNA
<213> ORGANISM: Streptococcus pneumoniae

<400> SEQUENCE: 19
tccctttctg gtaagatacc gtcacagtgt gaactttcca ctctc                         45

<210> SEQ ID NO 20
<211> LENGTH: 25
<212> TYPE: DNA
<213> ORGANISM: Human papillomavirus type 16

<400> SEQUENCE: 20
aactacatat aaaaatacta acttt                                               25

<210> SEQ ID NO 21
<211> LENGTH: 19
<212> TYPE: DNA
<213> ORGANISM: Human papillomavirus type 18

<400> SEQUENCE: 21
acctgggcaa tatgatgct                                                      19

<210> SEQ ID NO 22
<211> LENGTH: 22
<212> TYPE: DNA
<213> ORGANISM: Human papillomavirus type 33

<400> SEQUENCE: 22
```

```
tacatataaa aatgaaaatt tt                                            22

<210> SEQ ID NO 23
<211> LENGTH: 18
<212> TYPE: DNA
<213> ORGANISM: Human papillomavirus type 45

<400> SEQUENCE: 23
cctgtgccaa gtacatat                                                 18

<210> SEQ ID NO 24
<211> LENGTH: 50
<212> TYPE: DNA
<213> ORGANISM: Human papillomavirus unidentified type (ICPX1)

<400> SEQUENCE: 24
aactacatat aaaaatacta actttaagga gtacctacga catggggagg              50
```

GENOTYPING USING MULTIPLE VARIANT-SPECIFIC PRIMER POOLS

RELATED APPLICATIONS

This application is a continuation-in-part of U.S. patent application Ser. No. 10/623,458, filed 17 Jul. 2003, which claims the benefit of U.S. Provisional Pat. App. No. 60/399,357, filed 30 Jul. 2002. Both the of the foregoing applications are incorporated by reference, as if fully set forth herein, including any drawings.

FIELD

This invention relates to genomics, molecular biology, medical diagnostics and medicine.

BACKGROUND

The background information provided here is meant solely to assist the reader in understanding the current invention and the advances in the art provided thereby. Nothing in this section is intended, nor is it to be construed as, prior art to this invention.

In any genome, i.e., the accumulation of DNA that encodes the biological information in the form of genes that, along with environmental and developmental factors, determine the phenotype of all living things, there may be several kinds of genetically important allelic variations classified as insertions, deletions, single nucleotide polymorphisms (SNPs) and short tandem repeats (STRs). These variations may be harmless or they may give rise to serious potentially lethal disorders, which includes well-known diseases such as cystic fibrosis, sickle cell anemia, Tay-Sach's disease, hemophilia, Crohn's disease, heptatitis C, AIDS and cervical cancer.

With regard to disease-causing organisms, genotypic variation can result in either more or less serious infection and/or greater or lesser susceptibility to treatment, in general or with regard to specific treatment regimes. A prime but non-limiting example of this is Human Papillomavirus (HPV) for which over 200 genotypes are known. Of these, most relate to relatively benign problems, in particular warts. On the other hand a handful of HPV genotypes have been associated with cancer, particularly cervical cancer. These cancer-related genotypes have been subdivided into two groups, high-risk and low risk. The high-risk genotypes include HPV-16, 18, 31, 33, 35, 39, 45, 51, 52, 56, 58, 59, 66 and 68. The low-risk HPV genotypes include HPV-6, 11, 34, 40, 42, 43 and 44. It is not uncommon for an individual to be infected by several of these genotypes simultaneously. Each of these genotypes may, however, react very differently to specific treatment regimes. For example, the much-touted vaccine against cervical cancer-causing HPV is only effective against HPV 6, 11, 16 and 18, that is, two low-risk and two high-risk genotypes.

Another prime example of multiple variant pathogens is hepatitis C(HCV). HCV consists of 22 variants, 1a, b, c; 2a, b, c; 3a, b; 4a, b, c, d, e; 5a; 6a; 7a, b; 8a, b; 9a, 10a and 11a. These are all similar enough to be considered HCV but they are distinct genotypes.

The primary method of determining individual genotype(s) among a set of possibilities is to sequence DNA isolated from the source, i.e., from the viruses infecting a patient in the case of HPV.

DNA sequencing is typically accomplished using one of a number of procedures based on primer hybridization at or near a region of interest on a DNA, usually single-stranded. The hybridized primer is then extended over the region of interest followed by analysis of the resulting fragments to obtain the nucleotide sequence of the region of interest and, it is hoped, from that to identify the DNA and the source from which it was obtained.

Numerous sequencing techniques are known although most of them are based fundamentally on the Sanger dideoxy procedure, which harkens from 1975. The Sanger dideoxy procedure, however, requires the isolation of a sample containing a single DNA. Any more than that and the resulting data obtained are uninterpretable.

Sequencing by hybridization is also possible. In this technique, a pool of DNA whose sequence is to be determined is fluorescently labeled and hybridized to an array of known sequences. A strong hybridization signal from a particular location on the array identifies the unknown sequence as being present in the subject DNA.

It would be extremely beneficial to have a means of rapidly identifying one variant from among a possible plurality of variants or even more beneficial or essentially simultaneously and unambiguously identify more than one of the variants present. With regard to pathogenic organisms, this would permit rapid identification of variant-specific treatment regimes. The present invention provides such a means.

SUMMARY

Thus, in one aspect, the current invention relates to a method of identifying variants of an organism, comprising: providing a sample comprising a plurality of polynucleotides suspected of including one or more different polynucleotides, each of which has a target sequence unambiguously identifiable with one and only one variant of the organism; providing a pool of different oligonucleotide primers, each different primer being capable of hybridizing only to one of the variant-identifiable polynucleotides; mixing the sample and the pool of primers; subjecting the mixture to hybridization conditions; extending the hybridized primers; sequencing the extended primers without separating and isolating them; and analyzing the sequences, without separating or isolating them, to identify the variant(s) of the organism.

In an aspect of the invention, extending the primers comprises Pyrosequencing.

In an aspect of the invention, analyzing the sequences comprises pattern recognition.

In an aspect of the invention, the polynucleotides comprise DNA.

In an aspect of the invention. the polynucleotides comprise RNA.

In an aspect of this invention, the organism is selected form the group consisting of a bacterium, a fungus or a virus.

In an aspect of the invention, the bacterium, fungus or virus is pathogenic.

In an aspect of the invention, the virus is human papillomavirus.

In an aspect of the invention, the bacterium is selected from the group consisting of *Listeria* spp., *Staphylococcus* spp., *Streptomyces* spp., *Streptococcus* spp., *Haemophilus* spp., *Neisseria* spp., *Enterococcus* spp., *Eschericia* spp. and *Klebsiella* spp.

In an aspect of the invention, the pool of different oligonucleotide primers comprises two or more different primers, each different primer being capable of specifically hybridizing to a different polynucleotide that is unambiguously identifiable with a human papillomavirus variant selected from the group consisting of high-risk variants 16, 18, 31, 33, 35, 39, 45, 51, 52, 58, 59, 66, 68 and 69 and low risk variants 6, 11, 34, 40, 42, 43 and 44.

In an aspect of the invention, the pool of different oligonucleotide primers comprises five primers, one of which specifically hybridizes to a polynucleotide that is unambiguously identifiable with high-risk human papillomavirus variant 16, one of which specifically hybridizes to a polynucleotide that is unambiguously identifiable with high-risk human papillomavirus variant 18, one of which specifically hybridizes to a polynucleotide that is unambiguously identifiable with high-risk human papillomavirus variant 31, one of which specifically hybridizes to a polynucleotide that is unambiguously identifiable with high-risk papillomavirus 33 and one of which specifically hybridizes to a polynucleotide that is unambiguously identifiable with papillomavirus 45.

In an aspect of the invention, extending the primers comprises extending semi-conservative regions of the variant-identifiable polynucleotides.

In an aspect of the invention, one or more of the different polynucleotides is unambiguously identifiable with a minority variant of the organism.

In an aspect of the invention, one or more of the hybridized primers extends in low yield.

In an aspect of the invention, the different polynucleotides comprises one or more mutations of the organism.

In an aspect of this invention, the organism is human immunodeficiency virus (HIV).

In an aspect of the invention, the sample is obtained from a patient infected with the variant or variants of the organism.

DETAILED DESCRIPTION

Brief Description of the Figures

The figures are included solely for the purpose of assisting the reader in understanding the invention and are not intended nor shall they be considered as limiting the scope thereof in any manner whatsoever.

" In FIG. 5a, sequencing with the U3R general amplification primer is shown. In FIG. 5b, a two primer specific-primer pool is used. Using the primer pool, sequences of 19 and 31 bases which are stretches of similar nucleotide sequence are avoided.

DETAILED DESCRIPTION OF THE INVENTION

Discussion

Figure 1:
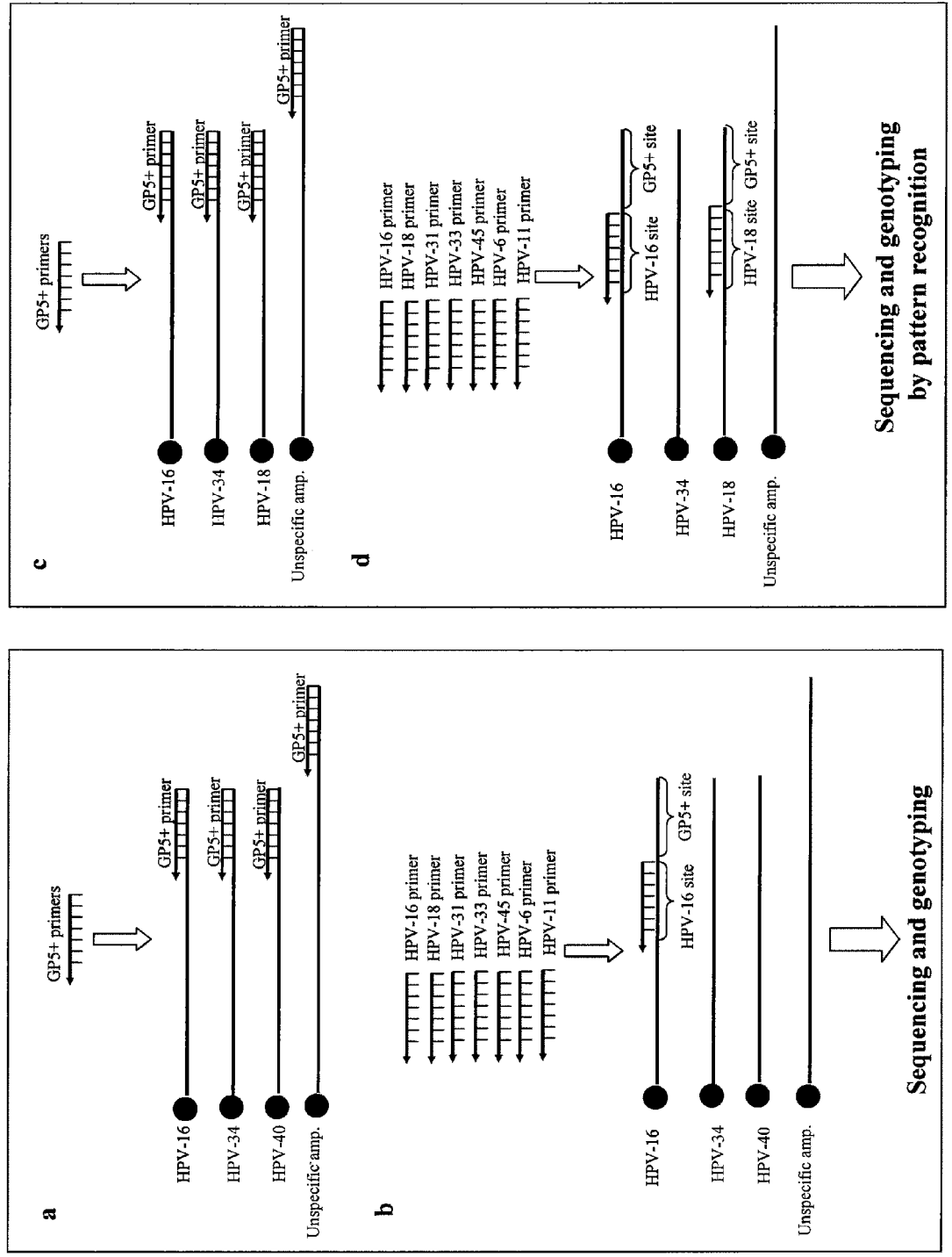
FIGS. 1a and 1c illustrates typing of HPV with more than one variant present using a general primer (FIGS. 1a and 1c)
FIGS. 1b and 1d illustrates typing of HPV with more than one variant present using a primer set of this invention.

It is understood that use of the singular throughout this application including the claims includes the plural and vice versa unless expressly stated otherwise. That is, "a" and "the" are to be construed as referring to one or more of whatever the word modifies. Non-limiting examples are: "a polynucleotide," which is understood to include one polynucleotide agent, two polynucleotides or, under the right circumstances as will become evident in the discussion that follows, even more polynucleotides unless it is expressly stated or is unambiguously obvious from the context that such is not intended. Likewise, "a biodegradable polymer" refers to a single polymer or a mixture of two or more polymers unless, again, it is expressly stated or absolutely obvious from the context that such is not intended.

As used herein, unless specified otherwise, any words of approximation such as without limitation, "about," "essentially," "substantially" and the like mean that the element so modified need not be exactly what is described but can vary from exact compliance with the written description by as much as ±15% without exceeding the scope of this invention.

As used herein, the term "simultaneously" is intended to covey the fact that multiple variants can be identified from a mixture that results from the methods disclosed herein with little, if any, intervening procedures or techniques separating the identifications. It is not intended nor is it to be construed that the identification of a number or variants from a single sample will occur at exactly the same time.

As used herein, the use of "preferred," "preferably," or "more preferred," and the like refer to modify an aspect of the invention refers to preferences as they existed at the time of the earliest filing date to which this invention is entitled.

As used herein, a "variant" refers to any genetically distinguishable variation of a given organism. The terms includes, without limitation, species, strains, mutations and genotypes depending on which term is usually applied by those skilled in the art to differentiate between genetically different but genomically-related entities. For example, without limitation, those skilled in the art often refer to genomically related bacteria as being species of a parent bacterium with variants being a subset of species. So long as two entities can be unambiguously identified from on another by virtue of a difference in the nucleotide sequence of at least one polynucleotide existing in all the related entities, the use of the method disclosed herein for performing that identification is within the scope of this invention. In many clinically relevant instances, a particular variant can be virulent, that is, can be associated with an "infection," for example, a bacterial infection such as that caused by methicillin-resistant *Staphylococcus aureus* or a viral infection such as cervical cancer-causing HPV variants.

As used herein, an "organism" refers to any living entity that comprises variants as set forth above. In particular, it refers to bacteria, fungi, viruses (even though some of those skilled in the art do not consider viruses to be "living"), protists and archaea.

As used herein, "genotyping," which normally is understood by those skilled in the art to refer to relate to revealing the complete genome of an organism, will be extended to refer to typing, detection and identification of variants.

The current invention relates to a method of identifying a single variant from among a plurality of variants through sequencing of unambiguously determinant polynucleotides, usually DNA or RNA, without the necessity of separating the polynucleotides before sequencing. This is accomplished using a multiple oligonucleotide primer pool with one primer being specific for each polynucleotide suspected of being among the plurality of polynucleotides obtained from the variants. The primers selectively hybridize to their specific polynucleotide and then are extended and the resultant amplicons are sequenced using pattern recognition.

Thus, identification of amplicons from a mixture of multiple variants of HPV amplified with consensus/degenerate primers can be hybridized en masse, extended, sequenced and the individual variants identified by pattern recognition. Generally, but not necessarily, the primer pool will contain primers specific for the high-risk HPV variants since these are the ones associated with cervical cancer.

Using the method herein, it can readily be determined if a clinical sample obtained from a patient contains none, one or several of the high-risk variants and a treatment regime can be formulated accordingly. A non-limiting example of this is illustrated in Fig I, where the consensus/general primer GP5+ was used to hybridize to each of four HPV variants and an unspecified polynucleotide and the result was uninterpretable whereas, using a seven-primer variant specific primer pool of this invention, only the HPV variant of interest, high-risk HPV-16 was hybridized, extended and sequenced and thereby easily identified. Similarly in FIG. 1, it is shown that using the consensus primer the same uninterpretable result is obtained when the sample contains DNA from two high-risk HPV variants but using the same seven-primer pool of this invention, which pool includes primers specific for HPV-16 and HPV 18 among others, only the DNA from those variants were hybridized, extended and sequenced and were likewise readily identified by pattern recognition.

Figure 2:
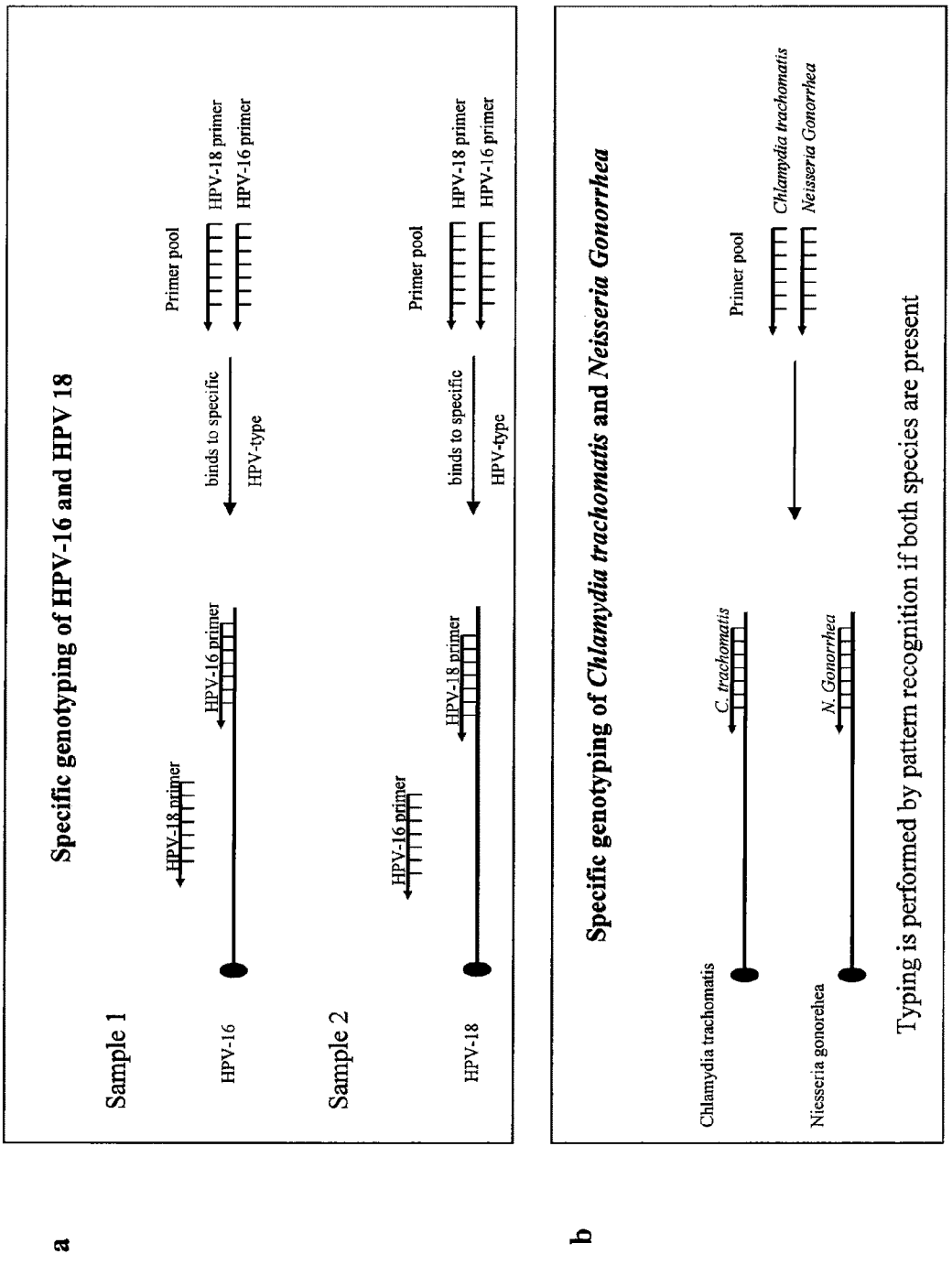
FIG. 2a illustrates the simultaneous variant specific genotyping of clinically important HPV 16 and HPV 18 using the method of this invention.
FIG. 2b illustrates typing of two bacterial species amplified by nested PCR using pattern recognition.

FIG. 2*a* further illustrates the above concept by illustrating the use of a two-primer pool, one primer specific for HPV-16 and one primer specific for HPV-18. If only one of the two variants is present, it will be hybridized to its specific primer, extended, sequenced and easily identified. If both variants are present, both will hybridize to their specific primers, both will be extended and sequenced and the resultant mixture can be readily analyzed using pattern recognition to confirm the presence of both high-risk variants. FIG. 2*b* illustrates the use of the method herein to reveal the presence of one or both the sexually transmitted disease (STD) causal agents *Chlamydia trachomatis* and *Neisseria gonorrhea* wherein DNA from the two species is hybridized using multiple sequencing primers of this invention and amplified by multiplex PCR.

Figure 3:
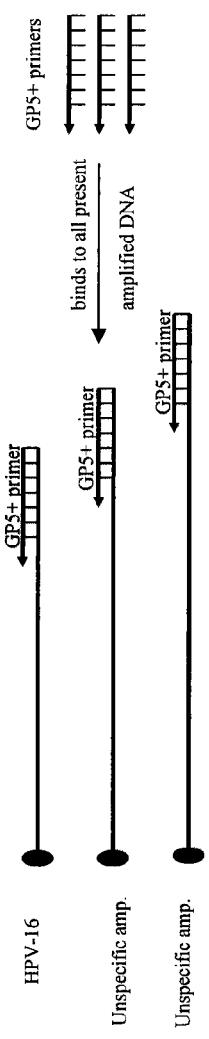
FIG. 3a illustrates typing amplicons containing unspecified amplification products sequenced using a general primer.
FIG. 3b illustrates typing amplicons containing unspecified amplification products sequenced using a variant-specific multiple sequencing primer pool of the invention.
Figure 3:
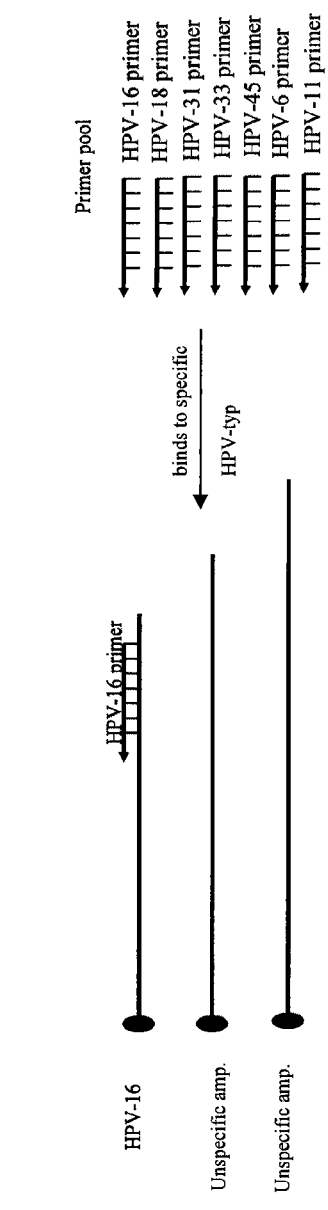

FIG. 3 further illustrates the power of the current method. In FIG. 3, a mixture containing high-risk variant HPV-16 DNA was mixed with several unspecified DNAs and subjected to the method hereof. If a consensus primer is used the result of hybridization/extension/sequencing is useless while if a seven-variant-specific primer pool is used, the presence of HPV-16 is easily determined.

Figure 5:
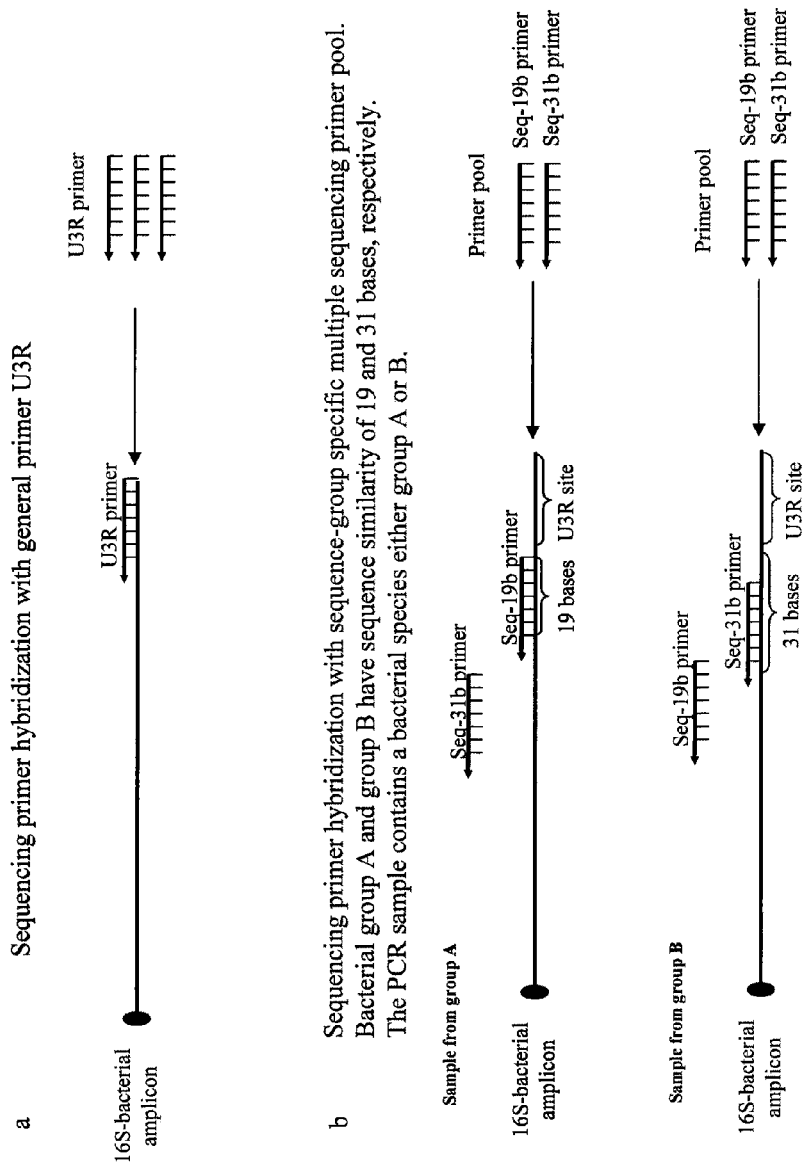
FIG. 5 is a schematic illustration of "winning read length.
Figure 6:
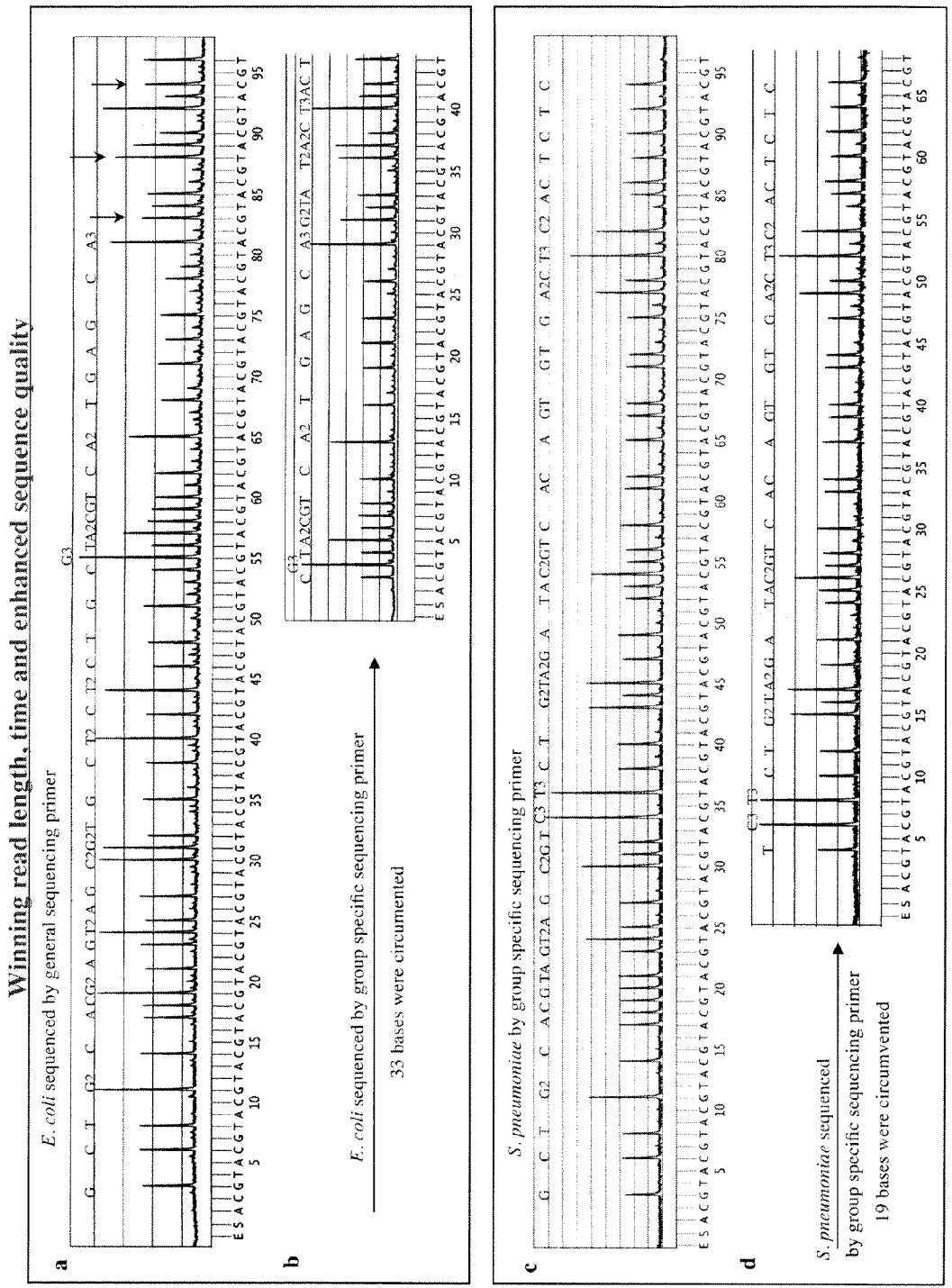
FIG. 6a is a pyrogram of *Escherichia coli* sequenced using a general primer.
FIG. 6b is a pyrogram of *E. coli* sequenced using a primer set of this invention whereby 31 bases of a semi-conserved region are by-passed.
FIG. 6c is a pyrogram of *Streptococcus pneumoniae* sequenced using a general primer.
FIG. 6d is a pyrogram of *Streptococcus pneumoniae* sequenced using a primer set of this invention whereby 19 bases of a semi-conservative region are by-passed.

FIG. 5 illustrates yet another major advantage of the current method. Shown in FIG. 5*a* is sequencing of a sample of bacterial DNA using the UR3 general primer. By necessity, the UR3 primer being a consensus primer must hybridize to at least a semi-conserved region of the bacterial DNA. It then must extend not only the region of interest for the purposes of distinguishing the two bacterial variants but also must extend the 19- and 31-base regions of sequence similarity. The result can be a significant decrease in sequence accuracy and quality. On the other hand, using a two-primer variant-specific primer pool of this invention, hybridization occurs much closer to the variant-defining region of the DNA and the well-known limitations in read length of DNA sequencing techniques are avoided resulting in faster, higher quality and more accurate sequencing of more of the region of interest with subsequent high reliability variant determination; i.e., a "winning read length." FIG. 6 further illustrates this feature. In FIGS. 6a and 6b, pyrograms obtained from the sequencing of E. coli are shown and it is evident that 33 bases irrelevant to the variant determination are avoided using the method of this invention. The same is shown in FIGS. 6C and 6d where pyrograms of the sequencing of S. pneumoniae is shown where 19 unneeded bases are avoided.

Figure 7:
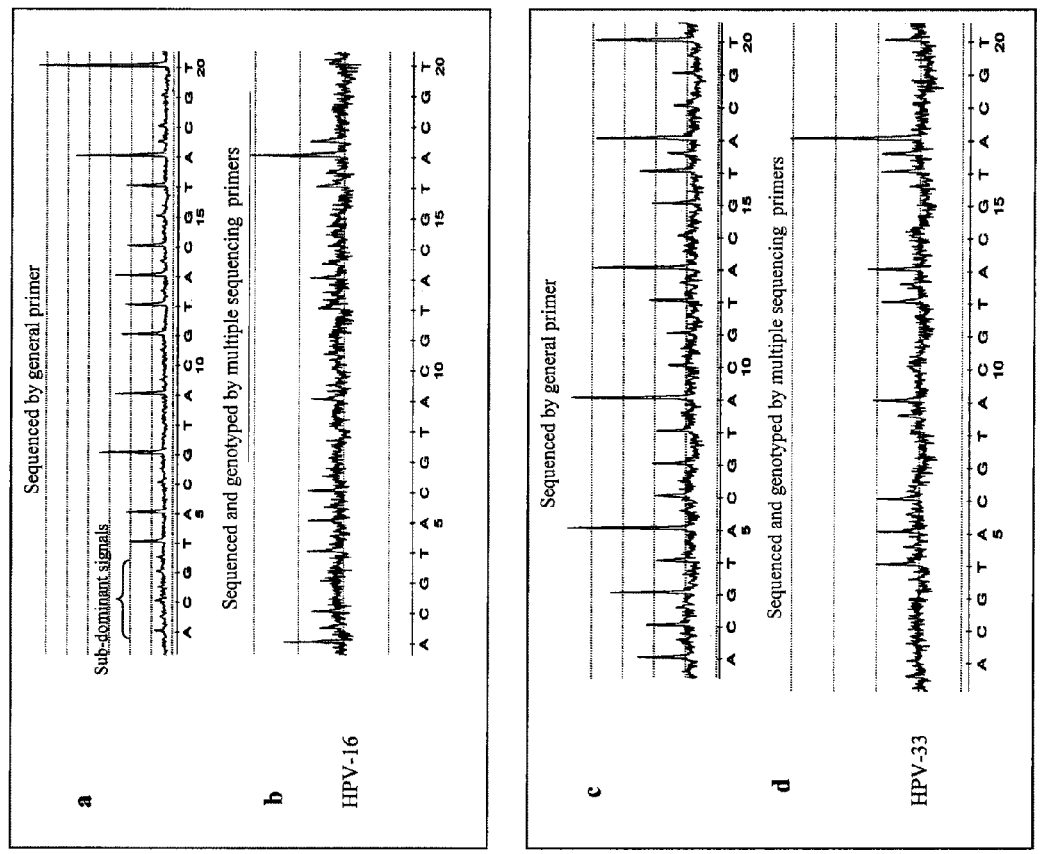
FIG. 7a shows the results of genotyping an HPV sample containing dominant multiple variants along with subdominant HPV-16 and unspecific amplification products sequenced using the general primer GPS+.
FIG. 7b shows the results of genotyping the sample of FIG. 7a using multiple sequencing primers of this invention. HPV-16 is still genotyped despite being subdominant.
FIG. 7c shows the results of genotyping an HPV sample containing multiple HPV variants including HPV-33 and unspecified amplification products amplified using PCR with the general primer GP5+.
FIG. 7d shows the results of genotyping the HPV sample of FIG. 7c using a multiple sequencing primer of this invention. HPV-33 is easily detected in spite of its low PCR yield.

Amplicons with low yield or amplicons containing sub-dominant types, which cannot be detected by current sequencing methods due to low sequence signals when in presence of the dominant sequence signals such as unspecific amplification product and/or or multiple dominant variants, can be readily identified using the method of this invention. Thus, FIG. 7a shows a clinical sample with extremely low sequence signals, which cannot be detected by the general sequencing primer due to unspecific amplification, but is easily detected using a variant-specific multiple sequencing primer pool of this invention. FIG. 7b illustrates the same principle using a clinical sample of a multiple variant infection where the PCR yield is low and the DNA is sequenced using a general primer, which fails to provide adequate information to identify the variants present and using a multiple variant-specific sequencing primer pool of this invention.

Thus it is clear that general/consensus primers used in PCR (especially in one-step PCR) tend to give unspecific amplification products since the primer will hybridize to all present amplified products in a sample, giving rise to mixed sequence signals from specific and unspecific PCR amplifications in the sequencing process and thereby making genotyping impossible (FIGS. 1 and 3).

Attempts have been made to improve the reach of various sequencing techniques. Pourmand et al., Nucleic Acids Res 30 (2002) disclose the use of a multiplex Pyrosequencing approach wherein the nucleotide identity of several different variable sites but only in a single variant are detected. Pourmand discloses the use of its approach for microbial typing of HCV based on hybridizing a pool of three oligonucleotides to one HCV variant on three different regions of that variant (not, as would be the case using the present invention on regions of different HCV variants). The primers are extended simultaneously on the same fragment by nucleotide addition and the resulting three sequence signals can be used to identify the specific HCV being studied. The idea behind this invention is to shorten required read length in DNA sequencing just as is done in the present invention but only for a single variant. Nevertheless, Pourmand does, by obtaining sequence from three regions of one variant simultaneously, offer a means for faster, more accurate HCV genotyping.

It should be understood that prior to the present invention multiple variant and unspecific amplifications present in one specimen was highly problematic to unambiguous detection by sequencing procedure. The variant-specific multiple sequencing oligonucleotide pool approach of this invention enables the skilled artisan to easily genotype samples comprising a plurality of variants or a single variant or, again, multiple variants confounded by unspecific sequence amplifications. That is, the multiple sequencing primer approach provides sequence data of high quality because of the specificity of the primers without interference from unspecific amplification products. Among other advantages the present method eliminate the need for special PCR techniques such as nested PCR or re-performing failed PCR or PCR cloning.

It is particularly significant that sequences representing a minority of total PCR product, which may remain undetected in a sample taken from a source containing one or more clearly dominant genotype(s). The multiple variant-specific sequencing primer pool method of this invention overcomes this shortcoming; sub-dominant variants are readily detected.

Likewise, when PCR products are obtained, for one reason or another, in low yield, it is difficult to detect the variants present when using general primer-predicated sequencing because signals from unspecific amplification products and/or multiple variants may interfere and the signals from the relevant genotype may go unnoticed. The multiple sequencing variant-specific primer pool method of this invention easily detects low yield fragments.

Figure 8:
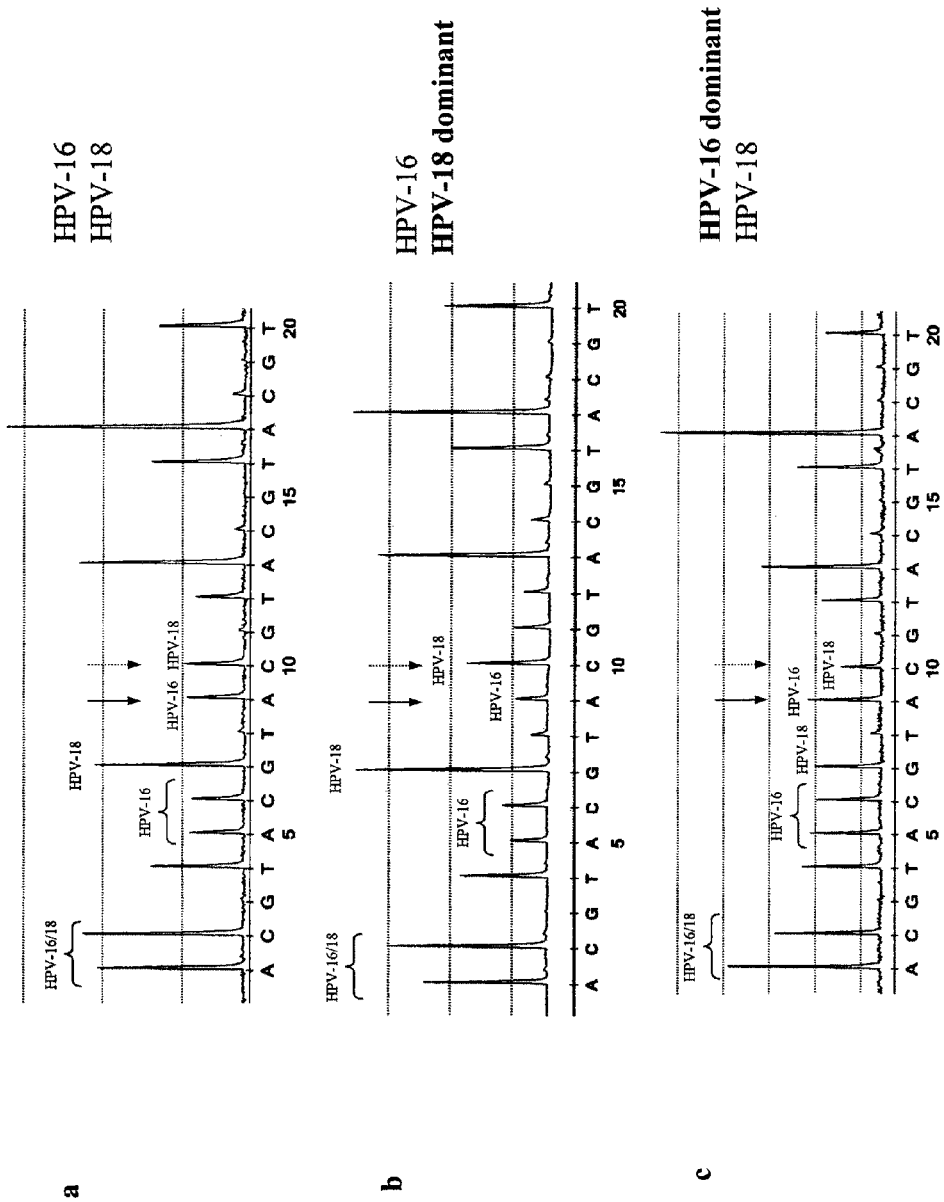
FIG. 8 shows the results of genotyping of three clinical samples containing HPV-16 and HPV-18 using a pool of seven multiple sequencing primers of this invention. Genotyping is performed by pattern recognition. The common and specific bases for each type is noted on top of each peak, characterizing each type, which facilitates genotyping. The dominant type could be easily observed by comparison of single bases shown by arrows: a) HPV-16 and HPV-18 almost equal in dominance b) HPV-18 dominant and c) HPV-16 dominant.

When the primers of a primer pool of this invention anneal to more than one variant in a sample, pattern recognition is used to detect all variants present. Pattern recognition is based on the sequence characteristics of each variant by sequence alignment. This is illustrated in FIG. 8 where clinical samples containing HPV-16 and HPV-18 in which either of the variants can be dominant or subdominant are readily identified using the method of this invention.

The primer pool used in the present invention is designed specifically for each sample type, depending on what sequences are expected to be present and which of those one wants to detect. The primer pool comprises at least two primers, wherein each primer is directed to a different, variant-specific sequence in the DNA of the target variants that might be present in the sample. Those skilled in the art will be able, based on the disclosures herein, to design and prepare such variant-specific oligonucleotide primer pools for a wide variety of microorganisms and the scope of this invention is not limited to the viruses and bacteria used to illustrate the invention. In using the method herein, genotyping of those variants will be faster more accurate and more reliable.

By using a primer directed to a conserved region, as is done in the prior art, it is impossible to distinguish between closely related, but ultimately distinguishable, variants present in a sample, since all the variants present will be sequenced. In contrast, by using a primer set according to the present invention, only the variants for which complementary primer(s) is (are) present will be sequenced and detected. Genotyping is thus simplified and accelerated. Use of the variant-specific primers also facilitates genotyping using shorter DNA reads—"a winning read length". Of course, when two or more genotypes are present, sequence pattern recognition can be used to identify the variants present.

The method can be used when unspecific amplification products, amplicons with low yield or amplicons containing sub-dominant types are present, again, because only the targeted DNA will be sequenced. This eliminates any need for nested PCR or cloning or re-performing failed PCRs. Another advantage of using a primer pool of the current invention is the ability to avoid reading conserved and/or semi-conserved regions of DNA in order to reach the variable regions which have to be sequenced in order for a typing to be performed. DNA-sequencing technologies have limitation in reading length, i.e., the number of the nucleotides that is possible to sequence from the position of the sequencing primer. Then, if a sequencing primer is designed for a conservative region, and the semi-variable region is positioned between the conservative region and the type-specific region of interest, the sequencing data from the type-specific region may be poor. However, if the sequencing primer, as in the invention, is designed for hybridizing to the semi-conservative region, the primer attaches closer to the variant-specific region. Thus, sequences comprising less informative data need not be read, and the sequencing data of the specific region will be obtained faster with higher sequence quality.

Generally, the method is carried out as follows: to a nucleic acid sample, preferably single-stranded DNA, is added a pool of primers comprising of two or more oligonucleotides, which of which is specific for a certain variant-identifying DNA in the sample. The sample material may be obtained from any type of microorganism known to occur in variants as defined herein. The oligonucleotide hybridizing to the polynucleotide (DNA) functions as a sequencing primer for a subsequent sequencing reaction. If the sample comprises a plurality of variants, genotyping will ultimately be done by pattern recognition. Pattern recognition can be further simplified by finding a sequence characteristic for each type when primer designing.

As noted above, the method of this invention has been applied to samples comprising several genotypes of HPV (in practice, it would not be known what genotypes are present in the sample). If the oligonucleotides of the set of primers of the invention are designed to only hybridize to diagnostically interesting oncogenic high-risk HPV genotypes and of one or more such genotypes are represented in the sample, at least one of the oligonucleotide primers will hybridize to that/those genotypes' DNA in the sample and will afford a characteristic sequence. If the same sample comprises more than one high-risk genotype of interest, the variants will be detected using pattern recognition. In this latter case, quantitative information (amount and types of high-risk virus in the sample) will be obtainable.

If the number of variants present is large, e.g., greater than about 12, pattern recognition may be carrier out using two sub-groups of multiple variant-specific primers.

Accordingly, in one embodiment the sample is suspected to comprise at least two variants chosen from a known set of types. In another embodiment, the sample is a multiple infection, i.e. multiple variant, sample. In still another embodiment, at least one primer is specific for a high-risk variant of a disease linked to the infectious microorganism.

There are over 200 known HPV-types. Of these a few are regarded as high-risk causing cervical cancer and head and neck cancer. HPV-16 is responsible for 50-60 percent of cases and HPV-18 for 10-20 percent. HPV-31, HPV-33 and HPV-45 are each accountable for approximately 5 percent each depending on demographic factors, and regions. The low-risk HPV types are not as virulent with regard to causing cancer. HPV-6 and HPV-11 are important low risk HPV variants for skin and genital warts. The known clinically important high- and HPV variants are 16, 18, 31, 33, 35, 39, 45, 51, 52, 58, 59, 66, 68 and 69 and the low-risk variants are 6, 11, 34, 40, 42, 43 and 44. The primers of the variant-specific primer pool of the invention are selected accordingly.

The method is also useful in the detection of variants of bacteria such as clinically important *Listeria* species (such as *Listeria* monocytogenes), *Staphyloococcus* species (such as *Staphyloococcus aureus, Staphyloococcus haemolyticus, Staphyloococcus pneumoniae*), *Streptococcus* species (such as *Streptococcus agalactiae, Streptococcus anginosus, Streptococcus intermedius, Streptococcus milleri, Streptococcus mitis, Streptococcus pneumoniae*), *Haemophilus* species (such as *Haemophilus influenzae*), *Neisseria* species (such as *Neisseria meningitidis*), *Enterococcus* species (such as *Enterococcus lecalis, Enterobacter cloacae*) *Escherichia coli* and *Klebsiella pneumoniae*. This list merely exemplifies bacteria having clinically important variants. This invention is applicable to any such bacteria. That is, a pool of primers comprising several oligonucleotides unambiguously identifiable with a particular bacterial variant can be added to a DNA, RNA or other distinguishing polynucleotide sample, at present preferably being single-stranded DNA, whereby only one of the oligonucleotides will hybridize to each polynucleotide identifiable with a particular variant in the sample, and thereby have the capacity to function as a sequencing primer, if, as a non-limiting example, Pyrosequencing is employed, or as an extension primer if, as a further non-limiting example, dideoxy sequencing is used. The primer that hybridizes will be specific for a semi-conservative region specific for this group of bacteria. By a "semi-conservative" region is meant a region, which distinguishes between different groups of bacteria. Further differences may occur within the group which requires the need for a variable region to be analyzed. One advantage with this aspect of the invention is to get shorter reads compared to that obtained using a general primer in order to get more sequencing data from the variable region.

It should be understood that the method herein can be used with a number of sequencing techniques but, at present, Pyrosequencing is preferred. As new and ostensibly better sequencing techniques become available, the multi primer pool approach of this invention will likely be amenable to that technique. As such, any sequencing technique presently known or any improved in those currently known techniques as well as any new techniques that become available in the future and that are found to be compatible with the method hereof are within the scope of this invention.

An interesting application of this current method is the detection of non-synonymous mutations in organisms. For the purposes of this invention, the difference between variants and mutations is that variants are relatively stable and tend to reproduce.

Synonymous or silent mutations are those that, although they can significantly alter nucleotide sequences in DNA and RNA and therefore the ability of primers to bind to polynucleotides containing such mutations compared to the unmutated version, do not alter the amino acid sequence of the protein derived from the DNA or RNA. Thus, they have no real effect on the biochemistry of the organism containing them. Non-synonymous mutations, on the other hand, do alter amino acid sequence often with serious consequences with regard to, without limitation, the virulence of the organism and/or the resistance of the mutated organism to existing treatment regimes. It would be extremely beneficial to be able to track non-synonymous mutational changes. Unfortunately conventional sequencing procedures such as the Sanger procedure would likely miss such mutations because the sequencing primer used may not hybridize to the mutated DNA/RNA. Using a multiple prime pool of this invention could avoid this problem by presenting a pool of primers containing numerous possible mutational sequences that could hybridize to the mutated polynucleotides. In this manner, it would be possible to characterize the entire mutant spectrum of an organism, which could represent a tremendous advance in the management of drug-resistant infections. A prime candidate for this application of the current invention would be the HIV, which is known to mutate rapidly and whose mutations are known to confound attempts to treat the disease.

Normally, analyzing variable regions with conventional sequencing technologies is a problem as there is a well-known limitation in read length (number of nucleotides that is possible to sequence from position of the extension or sequence primer) associated with DNA sequencing. If a sequencing primer is designed for a conservative region and a semi-variable region is positioned between the conservative region and the variable region of interest, the sequencing data from the variable region may be poor. However, if the sequencing primer, as in this invention, is designed for hybridizing to a semi-conservative region, the primer attaches closer to the variable region of interest. Then, sequences comprising less informative data need not be read, and the sequencing data of the variable region will be of better quality and the process is more time-effective. This applies for the entire DNA sequencing technologies as they have DNA read-length limitations.

The polynucleotide sample may beneficially be provided by isolation and purification of the sample. This may be accomplished by any conventional technique, many of which are known to those skilled in the art. During amplification, the nucleic acid molecules may be amplified with biotin-labeled primers or the like, in order to make it possible to bind the polynucleotides to a solid phase prior to typing. In this manner, it is possible to use the present method on double stranded DNA as described in Nordstrom, et al., Anal. Biochem., 2000, 282: 186-93 and Biotechnol. Appl. Biochem., 2000), 31(Pt 2): 107-12.

The set of primers in the current invention comprises at least two oligonucleotides. There is no absolute limit on the number of primers, the upper limit being determined by interferences or complications that may appear. For example, the primers might hybridize to each other, giving false sequence signals. This, however, may be avoided by using single strand binding protein (SSB) or extra wash (to remove the non-hybridized primers) or appropriate modification of the primers.

In order for a primer to be specific for a certain variant it is desirable that all nucleotides of the primer be complementary to the variant-specific region of it target variant. It varies from case to case how many nucleotides of the primer may be non-base-pairing yet still afford sufficient hybridization to occur. Generally, about 2-3 mismatches are enough to prevent sufficient hybridization. It is, however, most important that the extendable end (the 3'-end) of the primer hybridizes to the sample molecule, since otherwise extension may not be achieved.

If a primer is mis-hybridized (in extreme cases) in the hybridization step of the invention, binding to a different region of the target variant or another variant altogether, such will be revealed in the sequence data. For instance HPV-16 sequence data is specific only for HPV-16 and a different sequence data would reveal this problem. Thus, accordingly to the invention the risk for false positive results would be minimal using specific primer designs.

When a number of oligonucleotides are used together, they might interact such as by hybridization to each other, so called primer-dimer and get extended in the sequencing process such as by Pyrosequencing and may give rise to sequence signals. These signals could interfere with the DNA-sequencing. This problem can, however, be circumvented if the non-hybridized primers are removed by an extra wash prior to Pyrosequencing and/or single strand binding protein (SSB), which inhibits primer dimer(s), cross hybridization of primers or non-specific hybridization, is used.

Conditions allowing hybridization mean conditions wherein a variant-specific primer hybridizes specifically to its target variant without hybridizing to any other polynucleotide in a sample. A skilled artisan will be able to device such conditions based on the disclosure herein. Sequencing may be performed by any sequencing technique, preferably at present by conventional gel-based sequencing (e.g., without limitation, Sanger dideoxy sequencing), sequencing-by-synthesis, sequencing by mass spectrometry or any other DNA-sequencing protocol.

The polynucleotides obtained from the variants can be used directly from genomic DNA for the method of invention if the DNA sequencing technology is sensitive enough to circumvent PCR.

In one embodiment of the present invention at least one primer is specific for a high-risk variant of a disease linked to the infectious microorganism. In another embodiment the microorganism is HPV. Other applications are not excluded.

In one embodiment, the oligonucleotide primers of a kit of this invention are designed to be specific for any or all clinically important HPV variant, that is, any or all of high-risk HPV-16, 18, 31, 33, 35, 39, 45, 51, 52, 58, 59, 66, 68, 69 and/or low-risk HPV-6, 11, 34, 40, 42, 43, 44.

Kits can be developed for specific typing and sequencing of variants of interest or target DNA by DNA sequencing technologies. The kits could be used for genotyping and sequencing of variants of any manner of microorganism or virus or any other application requiring a multiple sequencing pool approach by DNA sequencing.

EXAMPLES

Example 1

Materials

The primers for Example I are designed for the HPV types that can be amplified with GP5+/6+ or MY09/11 primers sets. Each sequencing primer is designed to be specific for one designated HPV genotype. All the primers were checked by BLAST search for specificity.

The specific HPV-primers designed were, for high-risk HPV genotypes:

```
HPV-16      5'-GCTGCCATATCTACTTCAGA
HPV-18      5'-GCTTCTACACAGTCTCCTGT
HPV-31      5'-GTGCTGCAATTGCAAACAGT
HPV-33      5'-ACACAAGTAACTAGTGACAG
HPV-45      5'-TATGTGCCTCTACACAAAAT
``` and, for low-risk HPV genotypes:

```
HPV-6       5'-GTGCATCCGTAACTACATCTT
HPV-11      5'-GTGCATCTGTGTCTAATTCTG
```

The GPS+/6+ amplification primer set sequence is:

```
GP5+        5'-TTTGTTACTGTGGTAGATACTAC 3'
Biotin-GP6+ 5'-GAAAAATAAACTGTAAATCATATT C 3'
```

The MY09/11 amplification primer set sequence is:

```
Biotin-MY09  5'-CGTCCMARRGGAWACTGATC
MY11         5'-GCMCAGGGWCATAAYAATGG
```

Example 2

Typing of HPV in Clinical Samples and Simulated Mixed-Infections by Applying Multiple Sequencing Primers in Pyrosequencing Technology Some types of HPV are recognized on a global scale as causative agents for cervical cancer. They are also related to other cancer types. Pyrosequencing has been used previously for specific HPV-typing. In general, not more than 25 bases are needed for specific genotyping. Multiple infections, that is infection by multiple variants of HPV, and unspecific amplification have been a problem for typing as double/multiple variants or unspecific amplification products present in a sample will give rise to sequence signals from all available polynucleotides in the sample. This is mainly because, prior to the present invention, HPV variants were amplified using PCR with the general GP5+/6+ primer set and then sequenced utilizing GP5+ as the extension/sequencing primer. This primer hybridizes to all variants as well as unspecific sequences amplified by the GPS+/GP6+ general primer set (FIG. 1a and 1c illustrate this). The principle of the method of this invention is illustrated in FIG. 1b and 1d. That is, variant-specific oligonucleotide primers for high-risk HPV types are pooled and added to a multi-variant-containing (or, in the case of a clinical sample suspected multi-variant-containing) sample. If the sample contains one of the four oncogenic variants (16, 18, 33 or 45), one of the variant-specific oligonucleotide primers will hybridize to that variant and only to that variant. After hybridization the sample can be sequenced (with the hybridized oligonucleotide functioning as the extension/sequencing primer), and from the sequence the identity of the high-risk HPV variant can be determined.

Figure 9:
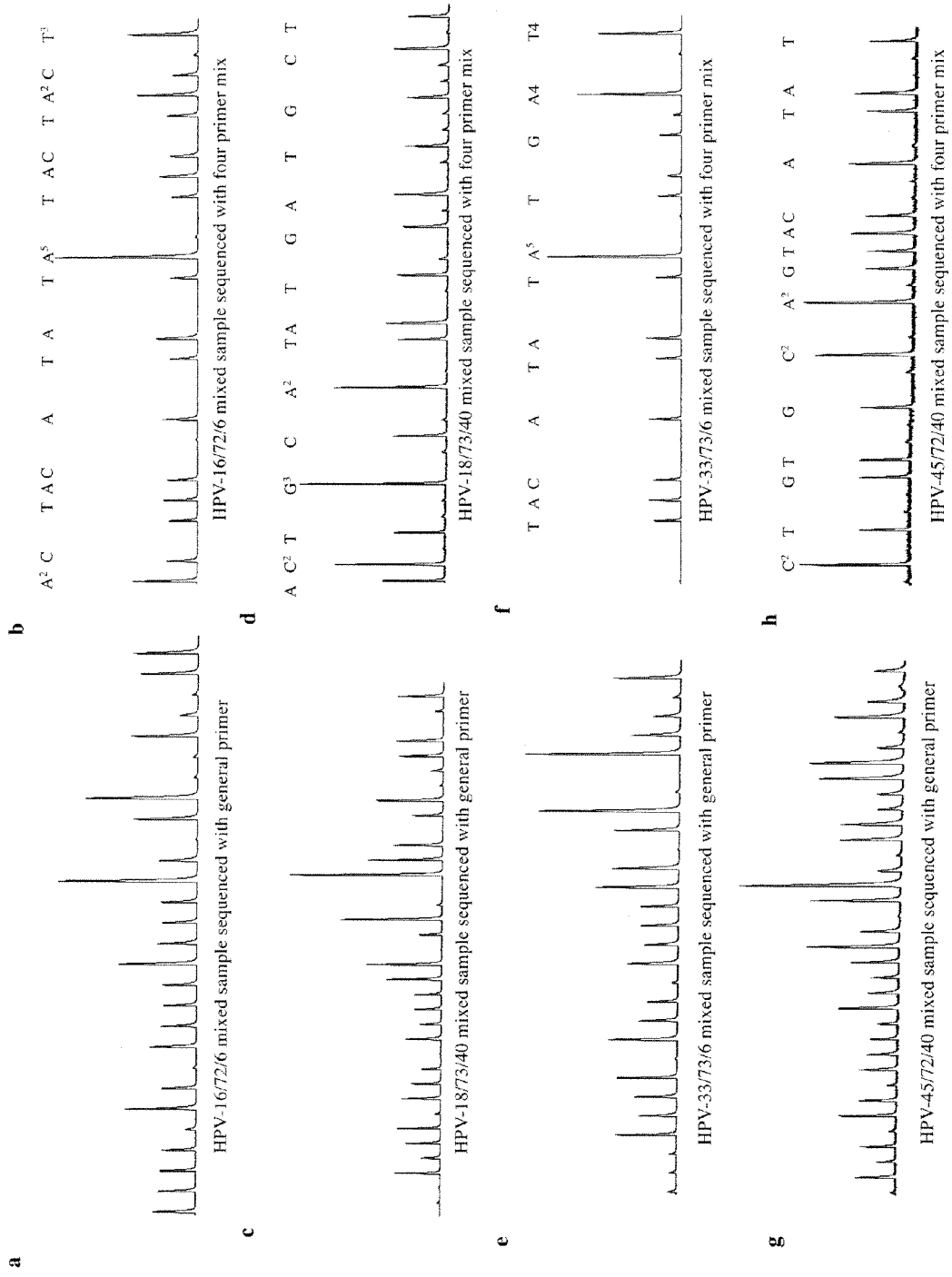
FIG. 9 comprises pyrograms of HPV samples having variants extended with general primer GP5+ (9a, 9c, 9e and 9g), which results in sequence signals from all present genotypes making genotyping impossible, and with (b, d, f, h) a four variant-specific primer pool for HPV-16, 18, 33 and 45. which results in specific sequence signals and therefore ready identification of these high-risk HPV-types.

Variant specific oligonucleotide primers were designed for detection of HPV-16, HPV-18, HPV-33 and HPV-45. Amplicons derived from HPV-6, HPV-16, HPV-18, HPV-33, HPV-40, HPV-45, HPV-72 and HPV-73 plasmid DNA (amplified with the general GP5+/6+ primer set), were mixed three and three in equal proportions (25 ul of each) prior to Pyrosequencing/dideoxy DNA-sequencing. Each triple-mix contained one high-risk and two low-risk variants. After single-strand separation of PCR products, the primer hybridization step was performed on each PCR-mix in two separate reactions; one reaction was hybridized with the GP5+ primer and the other with the specific four variant-specific oligonucleotide primer pool. The primed DNA samples were then sequenced 20-25 bases for genotyping with the Pyrosequencing technology. FIG. 9 shows typical traces from sequencing of the mixtures of HPV-16/72/6 (FIGS. 9a, 9b), HPV-18/73/40 (FIGS. 9c, 9d); HPV-33/73/6 (FIGS. 9e, 9f) and HPV-45/72/40 (FIGS. 9g, 9h) sequenced with the Gp5+ primer or the four variant-specific primer pool in two different reactions. The triple mixtures primed with GP5+ (FIGS. 9a, 9c, 9e and 9g) include sequence signals from three variants making genotyping almost impossible. On the other hand, the same triple mixtures primed with the four variant-specific oligonucleotide primer pool (FIGS. 9b. 9d, 9f and 9h) show variant-specific sequence signals and thereby can be correctly genotyped. The sequence data was analyzed with a BLAST search, and for genotyping of HPV-16, HPV-18, HPV-33 and HPV-45 no more than 18, 18, 20 and 17 bases were needed.

The same approach was repeated using a seven HPV variant specific primer pool on a series of simulated multiple variant samples and the expected variant-identifying results were obtained. The seven-sequencing primer-pool was also applied to 80 clinical samples amplified separately by GPS+/6+ (150 by fragments) and MY09/11 (450 by fragments) primer sets. A substantial number of the samples contained multiple variants or unspecific amplification products, which could not be genotypes using the GP5+ general sequencing primers. The multiple variants, however, could by easily genotyped using the method of this invention including pattern recognition. The dominance of each variant could be easily observed in multiple variant samples. FIG. 8 shows three different clinical samples containing multiple variants. The multiple variants were genotyped by pattern recognition. As there are seven sequencing primers used in this approach, one characteristic pattern is reserved for each genotype. For example, HPV18 is characterized by GGG in the 7th nucleotide addition and HPV-16 is characterized by the peaks for A, C and A, in the 5th and 6th and 9th nucleotide addition. FIG. 8 shows clearly these characterizations in HPV-16 and HPY-18 and the dominance of each genotype. HPV-16 and HPV-18 are the most common oncogenic genotypes and are found together in 70-80% cervical cancer specimens.

HPV genotypes that were minor constituents compared to either multiple variant or unspecific amplification products were also detected using the method of this invention. FIG. 7a shows a clinical sample containing HPV-16, which in this case is a minor constituent and not detectable by the general primer due to high sequence signals from either unspecific amplification products or multiple variant presence. Nevertheless it is genotyped by multiple sequencing primers despite its extremely low DNA concentration.

Amplicons with low PCR yield were also detectable and genotyped using the seven variant-specific primer pool. FIG. 7b shows oncogenic HPV-33 in a clinical sample, which is not detectable because of low yield using normal protocols but is detected and genotyped by the multiple sequencing primer technique of this invention. Multiple sequencing primers for HPV genotyping were applicable to both MY09/11 and GP5+/6+ derived amplicons.

Example 3

Figure 11:
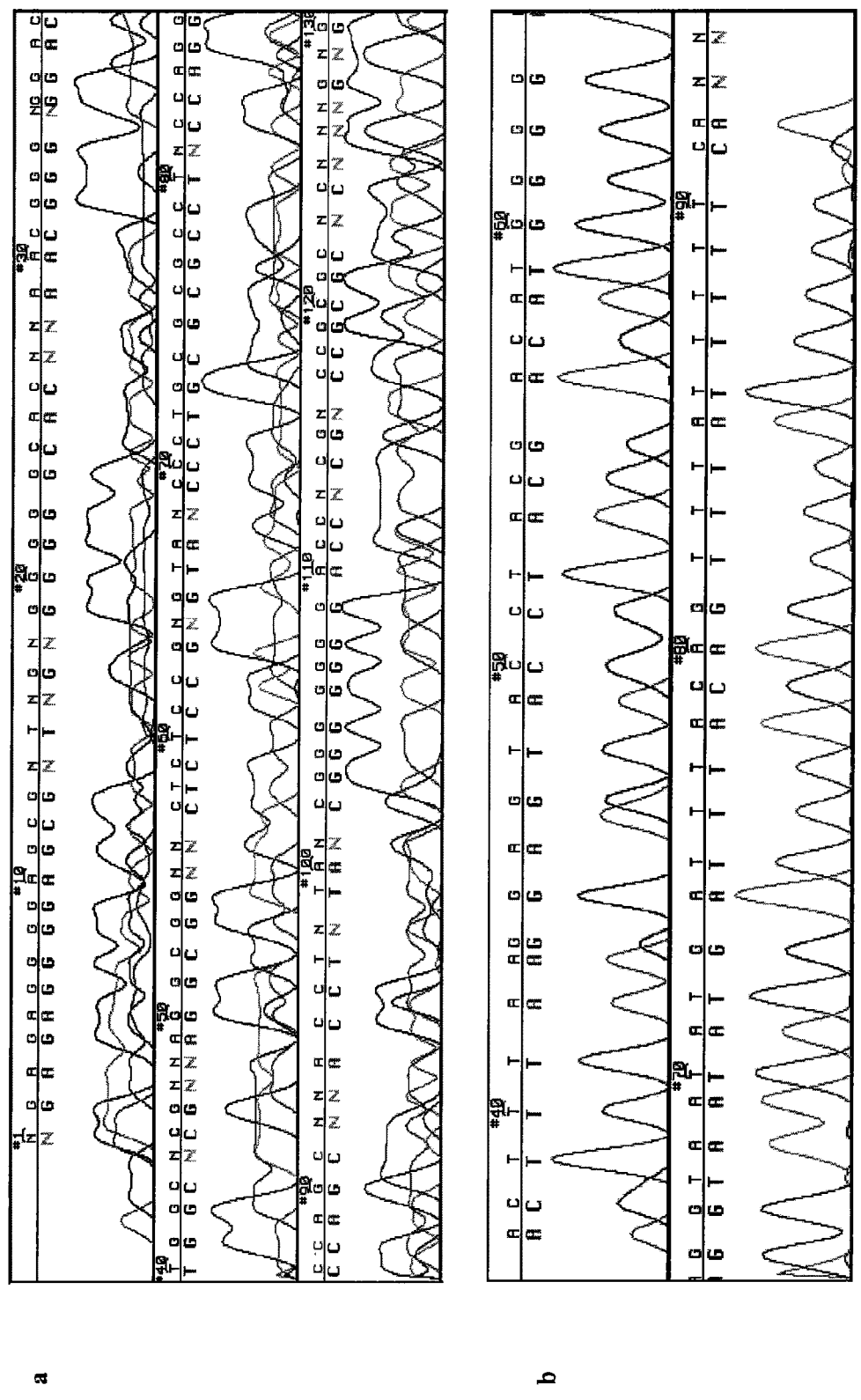
FIG. 11a is an electropherogram of a dideoxy sequenced sample containing multiple HPV variants HPV-16, 72 and 6, using GP5+ primer. The result is sequence data from all variants present making genotyping impossible.
FIG. 11b is another electropherogram of the sample in FIG. 11a but sequenced sample using a four-variant specific primer pool for high-risk HPV variants 16, 18, 33 and 45. Clear sequence signals were obtained indicating the presence of high-risk HPV variant 16 in the sample.

Typing of HPV in Mixed-Infections by Dideoxi DNA-Sequencing (Sanger) The general approach of Example 2 was repeated and Sanger sequencing was used as the DNA-sequencing method, instead of Pyrosequencing. FIG. 11a shows an HPV-16/72/6 mixture sequenced with a general primer as extension primer. FIG. 11b shows an HPV-16/72/6 mixture sequenced using a primer set of this invention, which comprises a pool of 4 primers (HPV-16, 18, 33 and 45). The results show clearly that, with dideoxy sequencing, genotyping with the primer set of the invention renders sequencing results that are readily interpretable whereas using the general primer method was uninterpretable. An ABI prism DNA analyzer 3700 (Applied Biosystems) was used for the DNA-sequencing with Big dye terminator kit following instructions in the manufacturer's manual. Same results were achieved on amplicons derived by MY09/11 using a-seven-multiple sequencing primers.

Example 4

Amplicons Containing Unspecific Amplification

Figure 4:
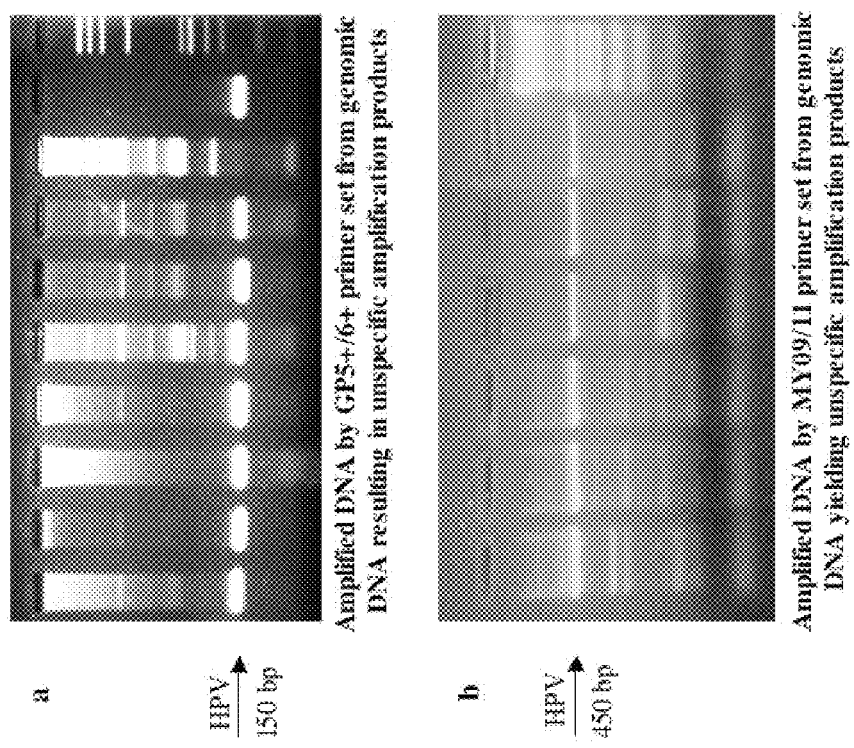
FIG. 4a illustrates the non-specific amplification of clinical samples from genomic DNA on ethidium bromide agarose stained gels using degenerate primers MY09/11. The result is uninterpretable.
FIG. 4b illustrates the non-specific amplification of clinical samples from genomic DNA on ethidium bromide agarose stained gels using general (consensus) primers GPS+/6+. Again, the result is uninterpretable.

GP5+/6+ and MY09/11 primer sets tend to yield unspecific amplification products from genomic DNA. FIG. 4 shows unspecific amplification products on agarose stained gels from amplicons derived from MY09/11 and GP5+/6+ primer sets. This, then, necessitates use of nested PCR for DNA sequencing and in some cases cloning to obtain any useable results.

Figure 10:
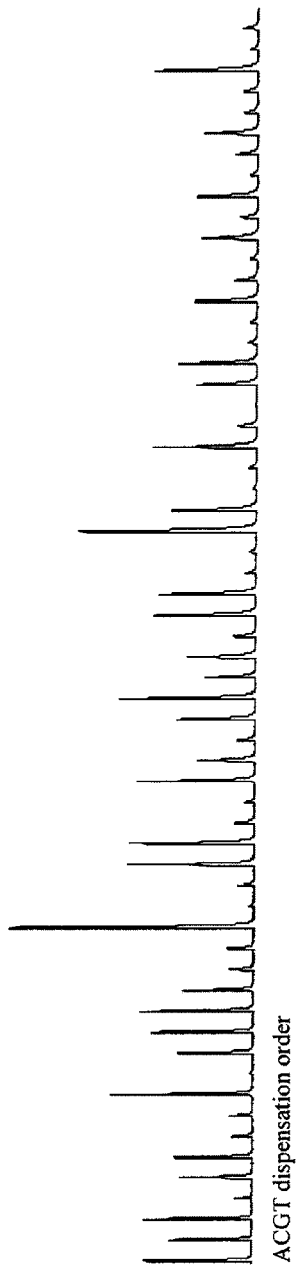
FIG. 10a is a pyrogram of a clinical sample amplified by GP5+/6+ consensus primer set in a one-step-PCR and sequenced using GP5+ primer. The result was an uninterpretable mixture containing numerous nonspecific sequence signals.
FIG. 10b is a pyrogram of the clinical sample of FIG. 10a where the amplified product was sequenced using a four-variant-specific primer pool for high-risk HPV variants 16, 18, 33 and 45. Clear sequence signals were obtained indicating that high-risk variant 16 was present in the sample.
Figure 10:
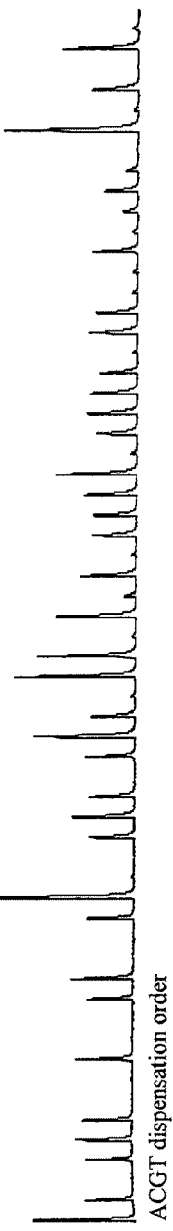

The GPS+ primer and the multiple sequencing pool of this invention were used for sequencing amplicons with one-step PCR containing unspecific amplification of clinical samples. The GPS+ sequence data were unclear with signals from unspecific products. FIG. 8a shows unspecific sequence signals from an HPV-16 amplicon primed with GPS+ (the same primer used in amplification), which make base calling and genotyping difficult. The sequence data using the multiple sequencing primer pool herein and the same amplicons with unspecific amplification were clear and specific. FIG. 10b shows specific genotyping of HPV-16 using the primer pool. The same sample was also amplified using nested PCR with primer sets MY09/11 and GP5+/6+. As shown in FIG. 10b (compare with FIG. 10a), clear sequence signal peaks were acquired by nested PCR. Thus, nested PCR or cloning can be totally avoided by using the multiple sequencing primer approach.

The same results were obtained on amplicons amplified directly by MY09/11. The majority of the samples contained unspecific amplification products when using MY09/11 PCR primer set. Good sequence results were obtained when using the multiple sequencing primer pool of this invention in the MY09/11-derived amplicon containing unspecific amplification products.

Example 5

Materials for Genotyping Bacteria

Extension/sequencing primers:

```
16S Seq-primer 19b
GCTGGCACGTAGTTAGCCG

16S Seq-primer 31b
GTTAGCCGGTGCTTCTTCTG
```

By using the above primers the sequences shown below could be avoided. Thus, in the first instance, it is not necessary to sequence 19 bases compared to conventional technology and in the second instance 31 bases need not be sequenced. The skipped sequences are:

```
GCTGGCACGTAGTTAGCCG
and
GCTGGCACGGAGTTAGCCGGTGCTTCTTCTG
```

Example 6

Winning Read Length and Typing of Bacteria by Pyrosequencing

The 16S rRNA gene has traditionally been used for typing of bacteria. In this procedure bacterial the 16S rRNA gene is amplified by PCR using general primers that bind to conservative regions of the gene. After single-strand separation, the immobilized single-strand DNA is primed with a general sequencing primer (e.g. U3R, see FIG. 5a). The sequence data obtained is analyzed by BLAST for identification. If Pyrosequencing is used for genotyping, the data obtained might not be sufficient. The reason is the limitation in read length obtainable by Pyrosequencing. The first region close to the primer site is semi-conservative and thereby less informative. Beyond this region a more variable region is reached, which is more useful for correct genotyping. For the purpose of using the method of this invention, the fact that microorganisms can be divided into groups, for which group-specific oligonucleotides can be designed, is used. This is illustrated in FIG. 5b. Group-specific oligonucleotide primers are pooled and added to a bacterial DNA sample amplified with PCR using general primers that bind to conservative regions on the 16S rRNA gene. At least one of the group-specific oligonucleotide primers will hybridize with the DNA (dependent on which groups are present). After hybridization, the sample can be sequenced and the bacterial type present in the sample can be correctly genotyped.

In a model system, group-specific oligonucleotide primers were designed for samples of bacteria that could be grouped in two categories; one group with a 19 bases sequence similarity after the PCR primer and the second group with 31 bases in common. FIG. 6b shows a pyrogram of *E. coli* sequence data circumventing the 31 bases-in-common using the multiple group-specific oligonucleotide primer pool of this invention. Bacterial 16S DNA was amplified with general primers Biotin U2F and U3R that bind to conservative regions on the 16S rRNA gene. After single strand separation, the immobilized single-strand DNA sample was hybridized with the pooled oligonucleotide primers herein. Fast and correct typing of bacteria from both groups was subsequently possible using Pyrosequencing. It is noted that in addition to the other obvious advantages of the method herein, sequencing data quality was improved. FIG. 6a shows an amplicon sequenced by the U3R general primer and group specific primers. The sequencing of 31 bases was circumvented and sequence quality was improved significantly by using the multiple sequencing primers herein (FIG. 6b). FIGS. 6c and 6d show *Streptococcus pneumoniae* amplicons sequenced by the U3R general primer and the pool of group specific primers. The sequencing of 19 bases was circumvented, making the DNA sequencing much faster.

The bacteria that can be effectively genotyped using the method herein include, without limitation, *Listeria* species, such as *Listeria* monocytogenes; *Staphylococcus* species such as *Staphylococcus aureus, Staphylococcus haemolyticus* and *Staphyloococcus pneumoniae*; *Streptococcus* species such as *Streptococcus agalactiae, Streptococcus anginosus, Streptococcus intermedius, Streptococcus milleri, Streptococcus mitis* and *Streptococcus pneumoniae; Haemophilus* species such as *Haemophilus influenzae; Neisseria* species such as *Neisseria meningitides; Enterococcus* species such as *Enterococcus fecalis* and *Enterobacter cloacae; Escherichia coli* and *Klebsiella pneumoniae*.

Example 7

Typing of Bacteria by Dideoxy DNA Sequencing

Figure 12:
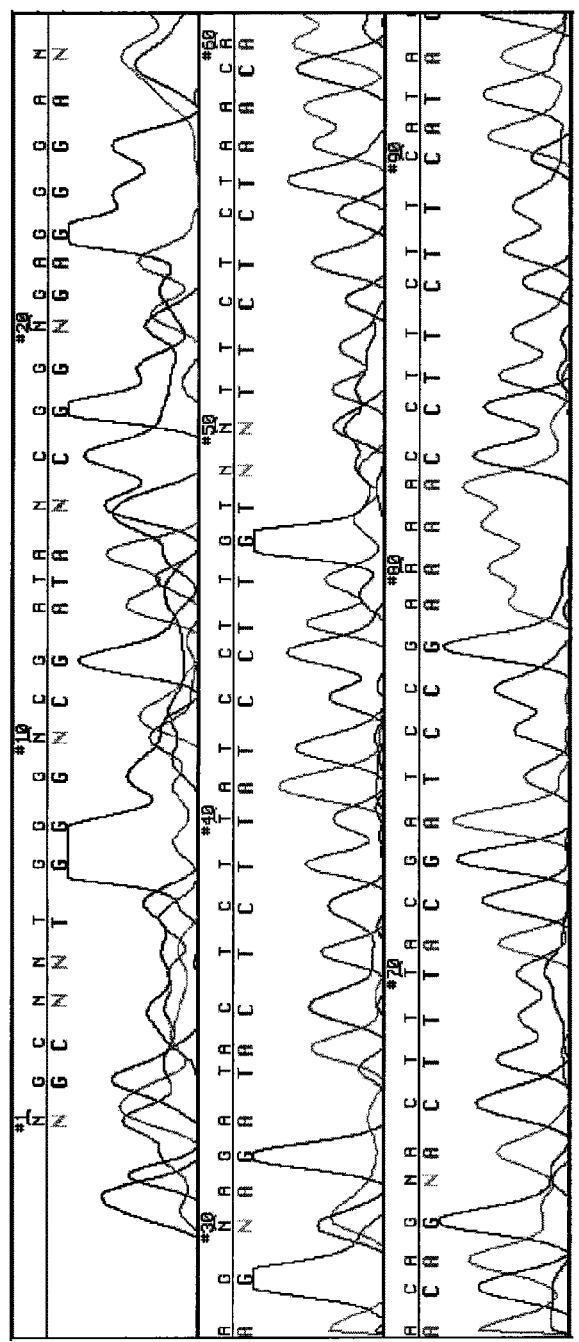
FIG. 12 is a Sanger dideoxy electropherogram of *Listeria monocytogenes* sequenced with a two-variant (Seq-19b and Seq-31b) specific primer pool.

The general approach of Example 6 was repeated, and dideoxy (Sanger) DNA sequencing was used as the sequencing method. The primer pool comprised 19b/31b (19b binds to *Listeria* monocytogenes, 31b binds to *Haemophilus influenzae*). The results show that Sanger sequencing is also suitable for genotyping using the primer pools of this invention. FIG. 12 shows sequencing of *Listeria* monocytogenes using a primer pool of this invention. An ABI prism DNA analyzer 3700 (Applied Biosystems) was used for the DNA-sequencing with the Big Dye terminator kit according to instructions in the manufacturer's manual.

What is claimed:

1. A method of identifying variants of an organism, comprising: providing a sample comprising two or more different polynucleotides, wherein: each different polynucleotide has a target nucleotide sequence that identifies that polynucleotide with a variant of the organism; providing a pool of different oligonucleotide primers, each different primer being capable of hybridizing only to one and only one of the above target nucleotide sequences; mixing the sample and the pool of primers; subjecting the mixture to hybridization conditions; extending the hybridized primers; sequencing the extended primers without separating or isolating the extended primers from one another, wherein sequencing the extended primers comprises pyrosequencing; and, analyzing the sequences by pattern recognition, without separating or isolating the sequenced extended primers from one another them, to identify the variant(s) of the organism.

2. The method of claim 1, wherein the polynucleotides comprise DNA.

3. The method of claim 1, wherein the polynucleotides comprise RNA.

4. The method of claim 1, wherein the organism is selected form the group consisting of a bacterium, a fungus and a virus.

5. The method of claim 4, wherein the bacterium, fungus or virus is pathogenic.

6. The method of claim 5, wherein the virus is human papillomavirus.

7. The method of claim 5, wherein the bacterium is selected from the group consisting of: *Listeria* spp., *Staphylococcus* spp., *Streptomyces* spp., *Streptococcus* spp., *Haemophilus* spp., *Neisseria* spp., *Enterococcus* spp., *Eschericia* spp. and *Klebsiella* spp.

8. The method of claim 6, wherein the pool of different oligonucleotide primers comprises: two or more different primers, each different primer being capable of specifically hybridizing to a different polynucleotide that is unambiguously identifiable with a human papillomavirus variant selected from the group consisting of high-risk variants 16, 18, 31, 33, 35, 39, 45, 51, 52, 58, 59, 66, 68 and 69 and low risk variants 6, 11, 34, 40, 42, 43 and 44.

9. The method of claim 8, wherein the pool of different oligonucleotide primers comprises five primers, one of which specifically hybridizes to a polynucleotide that is unambiguously identifiable with high-risk human papillomavirus variant 16, one of which specifically hybridizes to a polynucleotide that is unambiguously identifiable with high-risk human papillomavirus variant 18, one of which specifically hybridizes to a polynucleotide that is unambiguously identifiable with high-risk human papillomavirus variant 31, one of which specifically hybridizes to a polynucleotide that is unambiguously identifiable with high-risk papillomavirus 33 and one of which specifically hybridizes to a polynucleotide that is unambiguously identifiable with papillomavirus 45.

10. The method of claim 1, wherein extending the primers comprises extending semi-conservative regions of the variant-identifiable polynucleotides.

11. The method of claim 1, wherein one or more of the different polynucleotides is unambiguously identifiable with a minority variant of the organism.

12. The method of claim 1, wherein the different polynucleotide(s) comprises mutation(s) of the organism.

13. The method of claim 12, wherein the organism is human immunodeficiency virus.

14. The method of claim 1, wherein the sample is obtained from a patient infected with the variant or variants of the organism.

* * * * *